United States Patent [19]

Gibson et al.

[11] 4,381,223

[45] Apr. 26, 1983

[54] PROCESS FOR THE TREATMENT OF ORGANIC AMINE COMPOSITIONS

[75] Inventors: Charles A. Gibson; Moinuddin Ahmed; Michael Habenschuss, all of South Charleston, W. Va.

[73] Assignee: Union Carbide Corporation, Danbury, Conn.

[21] Appl. No.: 307,223

[22] Filed: Sep. 30, 1981

[51] Int. Cl.³ ............................................. B01D 3/00
[52] U.S. Cl. ..................................... 203/91; 564/503; 564/509
[58] Field of Search .................. 564/503, 509; 203/49, 203/91, 99, 6

[56] References Cited

U.S. PATENT DOCUMENTS 3,969,196  7/1976  Zosel ..................................... 203/49

Primary Examiner—Frank Sever
Attorney, Agent, or Firm—Jean B. Mauro

[57] ABSTRACT

This invention provides for the separation of an amine composition undergoing processing at high temperatures and pressures which amine composition contains volatile components and less volatile components where the volatile components are desirable for further processing and/or utilization and the less volatile components are less desirable for further processing and/or utilization. The separation serves to divide the amine composition into two streams, one which is enriched in the volatile components and the other which is enriched in the less volatile components.

6 Claims, No Drawings

PROCESS FOR THE TREATMENT OF ORGANIC AMINE COMPOSITIONS

BRIEF SUMMARY OF THE INVENTION

TECHNICAL FIELD

The invention relates to the treatment of organic amine compositions which are undergoing processing and maintained at relatively high temperatures and pressures. Such amine compositions are characterized by the fact that with time at least a portion of the components thereof can undergo molecular change and such amine compositions contain desirable components and undesirable components, the desirable components being more volatile than the undesirable components. The invention involves arresting such molecular change by subjecting the amine composition to a component separation at a pressure and temperature not substantially different from the pressure and temperature of the aforesaid organic amine composition prior to the time that such change occurs. This will result in forming from the separation two enriched streams, one which is more enriched in the more volatile amine components of such amine composition than is such amine composition. The other stream which is formed is less rich in such more volatile amine components than is said other stream and such amine composition but more enriched in the less volatile components of the amine composition than is either said other stream and the amine composition.

BACKGROUND ART

No prior art has been found which deals with the separation of an amine composition undergoing processing at high temperatures and pressures which amine composition contains volatile components and less volatile components where the volatile components are desirable for further processing and/or utilization and the less volatile components are less desirable for further processing and/or utilization, and in which the separation occurs at essentially the same pressure and temperature as the amine composition and serves to divide the amine composition into two streams, one which is enriched in the volatile components and the other which is enriched in the less volatile components.

DISCLOSURE OF INVENTION

This invention relates to the treatment of amine containing compositions while undergoing processing at high temperatures and pressures. In particular this invention relates to the treatment of an organic amine composition which while undergoing processing at high temperatures and pressures are susceptible to molecular change. More particularly this invention is concerned with the treatment of organic amine compositions while undergoing processing at high temperature and pressure so as to arrest any significant amount of molecular change therein and to separate therefrom those components which are regarded to be desirable and those components which are considered to be undesirable. In the most specific embodiment of the invention, the desirable components are the more volatile constituents or components of the organic amine composition and the undesirable components are the less volatile constituents or components of the composition.

The present invention provides a process for the treatment of organic amine compositions which are under such temperature and pressure that with time at least a portion of the components thereof can undergo molecular change and which can change desirable components and undesirable components, the desirable component being more volatile than the undesirable component, which comprises arresting such molecular change by subjecting such amine composition to a component separation at a pressure and temperature not substantially different from the pressure and temperature of said organic amine composition, prior to the time that such change occurs, forming from such separation two enriched streams, one which is more enriched in the more volatile amine components of such amine composition than is such amine composition, and the other of which is less rich in such more volatile amine components than is said other stream and such amine composition but more enriched in the less volatile components of the amine composition than is either said other stream and the amine composition.

DETAILED DESCRIPTION

The process of this invention may be practiced in any operation involving the utilization of an amine composition which contains a variety of different molecular components therein, some of which are more volatile than others and in which the volatile components are desirable for further processing and/or utilization. The process of this invention is particularly desirable where such amine compositions which are undergoing processing at high temperatures and pressures such that the amine composition can undergo change over a given period of time while maintained at such temperatures and pressures. For example, the process of this invention may be utilized in the treatment of fatty acid amides, amines from reduced fatty acids, mixtures of alkanolamines, mixtures of ethyleneamines, and/or mixtures of polyethyleneamines, and the like.

The process of this invention finds application in the treatment of amine compositions which can be produced by one or more of various technologies. For example, the process of this invention can be utilized in the treatment of alkanolamines formed by the reaction of alkylene oxides and ammonia or amines. It can be used in the treatment of ethyleneamines formed by the reaction of alkanolamines and ammonia or amines or by the reaction of ammonia or amines with alkanedihalides, such as ethylene dichloride. The process may be useful in the treatment of fatty acid amides such as those formed by the reaction of fatty acids their anhydrides or acid halides, with ammonia or amines. The process is also applicable to the treatment of fatty amines such as those formed by the reaction of fatty alcohols with ammonia or amines in the presence of a hydrogenation catalyst. The process also finds application to the treatment of amines which are formed by the hydrogenation of organic nitriles.

The common denominator in all of the above processes which determines the utilization of the process of this invention is the fact that at one point or another in those processes there exists organic amine compositions at elevated temperatures and pressures and such organic amine compositions have a varying molecular weight distribution which is subject to change over a period of time. In the typical cases, such compositions will be at a temperature in excess of about 100° C. and at pressures in excess of about 100 psia. The process of this invention allows for the treatment of these amine compositions in order to remove therefrom more valuable and more volatile constituents in such a manner as to arrest any significant molecular change of that constituent and allow for its subsequent utilization or treatment with the minimum change having occurred to that constituent prior to such utilization or further treatment.

In a preferred embodiment of this invention, the amine composition is subjected to the aforesaid component separation at a pressure and temperature at which such more volatile component becomes, during separation, a supercritical fluid. Supercritical fluid, as understood in the instant invention, refers to any fluid which is above its critical pressure. This means that during the separation treatment, the amine composition is caused to be converted into a multi-phase stream in which the volatile stream's composition is sufficiently altered, coupled with the temperature and pressure existing during separation, so as to exceed its critical pressure and such volatile component phase becomes a supercritical stream during the separation, thereby facilitating the separation. This is particularly the case where there is provided in combination with the amine composition that is undergoing change a potentially soluble gaseous component such as ammonia which allows for the control of the composition during the phase separation thereby to enhance the attainment of the supercritical fluid state. By adjusting the concentration of ammonia in the amine composition it is possible to facilitate reaching the supercritical state condition. However, the invention is not limited to achieving the supercritical state for the more volatile phase that is removed during the separation step. The invention also encompasses utilizing a gaseous component during the separation of liquid phases to enhance the removal of the more volatile liquid components from less volatile liquid components of the amine composition. In this aspect of the invention, ammonia will be soluble in the more volatile liquid phase and assists in its removal from the less volatile phase produced by the separation of the less volatile components.

In respect to achieving a supercritical fluid as pointed out above or in effecting separation of two liquid phases, where ammonia is utilized to enhance the separation, in both cases ammonia should form a homogeneous phase with the more volatile component being removed. By this, it is meant that ammonia does not become a further distinct phase from the more volatile component such as a vapor phase not in association with the more volatile component. That would occur in simple flash evaporation where the ammonia, because it is an extremely volatile material, would be rapidly removed from association with the organic amine composition undergoing separation at a much more rapid rate than would the more volatile component of that composition. Consequently, in flash distillation a homogeneous phase between ammonia and the more volatile component being separated would not occur as it does in the practice of this invention.

In the practice of the invention where the separation achieves a supercritical state for the more volatile component being separated, such as when ammonia is utilized to enhance such separation, such composition either as a supercritical fluid or as a liquid having ammonia dissolved therein may be readily transported in smaller piping and smaller pumps as compared to what would have to be utilized if the ammonia were to be separated as a vapor component as it occurs in flash distillation.

Thus in the practice of this invention during the separation, the more volatile component is either in the liquid state or is in the supercritical fluid state. The separation is not as effective if any of the volatile components were to be separated as a vaporous component, particularly so as a non-homogeneous component along with other volatile components being separated from a less volatile phase.

The separation of this invention can be carried out in any one of a number of types of separators. For example, the separation can be initiated in a tube or pipe which is connected to a tank in which the major portion of the separation occurs and the distinct phases are optimized. A convenient separation system involves feeding the amine composition through a pipe while either reducing or raising its temperature to that which is desired within the separator and thereafter feeding the amine mixture into the separator. The separator may be simply an empty tank that is empty in respect to any separation device such as trays, screens, packing and the like. Frequently, if it is possible that particles or droplets of material can be captured in the more volatile phase being separated then the more volatile phase should be passed through a demister pad so as to assure that such particles are not carried off out of the separation vessel, with the more volatile phase. The separation vessel should have a size which is large enough to handle the flow of organic amine thereto and should not be so oversized as to adversely affect the desired separation. In the operation of such a vessel, the more volatile components will be removed from an upper portion thereof and the less volatile component will be removed from a lower portion thereof.

The separator used in the Examples appearing hereinafter can be described as follows:

DESCRIPTION OF SEPARATOR

The separator is a 316 stainless-steel Karbate displacer manufactured by Magnetrol International, 5300 Belmont Road, Downers Grove, Ill., 60515. The separator is a sealed head model (Model A-3013) consisting of a switch housing with a heavy duty Type S-1 mercury switch mechanism therein and a fabricated carbon steel float chamber with an internal Karbate graphite displacer therein. The internal trim of the separator includes a displacer support spring, stainless-steel trim parts and a stainless-steel magnet attractor. This particular model is rated for use with 0.4 specific gravity liquid and rated at a maximum pressure of 5000 psi at 200° C. Dimensions of the separator are as follows: total length from top of switch housing to bottom of float chamber is 25.38 inches; length from top of switch housing to center of outlet fitting located on side of float chamber is 10.50 inches; length from top of switch housing to center of inlet fitting located on side of float chamber is 14.0 inches; length from center of outlet fitting to center of inlet fitting was modified from 11.50 inches (standard) to 3.50 inches for the specific examples illustrated hereinbelow; length from the center of the outlet fitting to the bottom of the float chamber is 14.88 inches; and length from the center of the float chamber directly to the outside edge of either the side inlet fitting or side outlet fitting is 3.88 inches. A bottom outlet fitting is located centrally at the bottom of the float chamber.

The operating principle of the separator used in the Examples appearing hereinafter can be described as follows:

OPERATING PRINCIPLE OF SEPARATOR

A solid displacer (graphite) which is heavier than the liquid entering the float chamber through the side inlet fitting rests its weight on a compression spring. The rising liquid level in the float chamber imparts buoyancy to the graphite displacer allowing the spring to move upward. A magnet attractor in the switch mechanism, attached to the spring, moves upward into the field of a permanent magnet. The magnet motion tilts a mercury switch in the switching mechanism for actuation. A non-magnetic barrier tube located in the switch housing provides a static seal between the switch mechanism and the graphite displacer assembly. The displacer type mechanism for liquid level control is an off-on instrument with an abrupt action. The switching mechanism was modified to include a solenoid for receiving a signal from the displacer type mechanism for the specific examples illustrated hereinbelow. The separator maintains a liquid level of 100 milliliters and activation with resulting liquid removal through the bottom outlet fitting occurs after an additional 180 milliliters of liquid is accumulated. The overhead product portion is removed continuously from the separator through the side outlet fitting.

EXAMPLES I THROUGH VI

Enrichment of Monoethanolamine in Overhead Volatile Effluent from the Separator

A reaction system and apparatus consisting of a separator identical to that described hereinabove were used in Examples I through VI. The separator was adjusted to an initial temperature of 175° C. and an initial pressure of 2300 psig. A liquid feed stream entering the separator was also adjusted to a flow rate specified for each Example in Table A below. The liquid feed stream in each Example consisted of ammonia (81.68 percent by weight), monoethanolamine (15.17 percent by weight), diethanolamine (1.65 percent by weight), triethanolamine (0.31 percent by weight) and water (1.19 percent by weight). The molar ratio of ammonia to ethanolamines (mono-, di- and tri-) was 18:1 for each Example. The initial temperature and pressure were then carefully adjusted in the separator until phase separation occurred, i.e., the liquid feed stream was separated into an overhead volatile portion and an underflow less volatile portion. The temperature and pressure at which phase separation occurred are given in Table A for each Example in addition to the production rate of the underflow less volatile portion expressed as percent by weight of the total feed stream. A sample of the overhead volatile portion removed from the separator as a supercritical fluid and a sample of the underflow less volatile portion removed from the separator as a liquid were then collected and analyzed by gas chromatography. The relative amount of each component contained in the overhead volatile portion and the underflow less volatile portion for each Example is given in Table A. Monoethanolamine, diethanolamine and triethanolamine are each expressed as percent by weight of the total ethanolamine concentration in the liquid feed stream, overhead volatile portion and underflow less volatile portion.

TABLE A
ENRICHMENT OF MONOETHANOLAMINE IN OVERHEAD VOLATILE EFFLUENT FROM THE SEPARATOR PROCESS DATA

| Example | I | II | III | IV | V | VI |
|---|---|---|---|---|---|---|
| Phase Separation Conditions | | | | | | |
| Temperature, °C. | 159.5 | 156 | 161 | 164 | 165.5 | 155 |
| Pressure, psig | 2035 | 1960 | 2100 | 2100 | 2160 | 1855 |
| Feed Stream | | | | | | |
| Flow Rate, grams/hr | 4150 | 4158 | 4086 | 3964 | 4199 | 2718 |
| Ammonia, grams | 3390 | 3396 | 3337 | 3238 | 3430 | 2220 |
| Ethanolamines, grams | 711 | 712 | 700 | 679 | 719 | 466 |
| Monoethanolamine, wt. % | 88.56 | 88.56 | 88.56 | 88.56 | 88.56 | 88.56 |
| Diethanolamine, wt. % | 9.63 | 9.63 | 9.63 | 9.63 | 9.63 | 9.63 |
| Triethanolamine, wt. % | 1.81 | 1.81 | 1.81 | 1.81 | 1.81 | 1.81 |
| Water, grams | 49 | 50 | 49 | 47 | 50 | 32 |
| Overhead Volatile Portion | | | | | | |
| Production Rate, grams/hr | 3802 | 3813 | 3864 | 3631 | 3805 | 2501 |
| Ammonia, grams | 3249 | 3286 | 3240 | 3149 | 3190 | 2182 |
| Ethanolamines, grams | 498 | 491 | 558 | 445 | 568 | 251 |
| Monoethanolamine, wt. % | 89.92 | 89.43 | 89.12 | 89.98 | 90.22 | 94.82 |
| Diethanolamine, wt. % | 8.55 | 8.86 | 9.15 | 8.48 | 8.24 | 4.58 |
| Triethanolamine, wt. % | 1.53 | 1.71 | 1.73 | 1.54 | 1.54 | .60 |
| Water, grams | 55 | 36 | 66 | 37 | 57 | 68 |
| Underflow Less Volatile Portion | | | | | | |
| Production Rate, grams/hr | 240 | 269 | 222 | 342 | 394 | 222 |
| Ammonia, grams | 51 | 69 | 70 | 95 | 167 | 60 |
| Ethanolamines, grams | 179 | 187 | 143 | 235 | 217 | 157 |
| Monoethanolamine, wt. % | 85.42 | 85.74 | 84.94 | 85.64 | 83.95 | 86.26 |
| Diethanolamine, wt. % | 11.91 | 11.63 | 12.31 | 11.80 | 13.10 | 11.29 |
| Triethanolamine, wt. % | 2.67 | 2.63 | 2.75 | 2.56 | 2.95 | 2.45 |
| Water, grams | 10 | 13 | 9 | 12 | 10 | 5 |
| Weight % of Feed Stream | 5.78 | 6.47 | 5.43 | 8.63 | 9.38 | 8.17 |

Examples I through VI illustrate the enrichment of monoethanolamine in the overhead volatile effluent from the separator. A phase separation which provides about 5 percent by weight to about 10 percent by weight of the total feed stream as underflow non-volatile portion increases the percent by weight of monoethanolamine in the overhead volatile portion up to about 7 percent by weight based on the total weight of ethanolamines (mono-, di- and tri-). Since the separator operates essentially as a single-stage flash-tank, proportionately more of the diethanolamine and triethanolamine content is taken as underflow non-volatile portion to increase monoethanolamine content in the overhead volatile portion. See Example VI in which monoethanolamine is enriched from 88.56 percent by weight in the feed stream to 94.82 percent by weight in the overhead volatile portion. Corresponding to the enrichment of monoethanolamine in the overhead volatile portion in Example VI, diethanolamine and triethanolamine are enriched in the underflow non-volatile portion, i.e., diethanolamine is enriched from 9.63 percent by weight in the feed stream to 11.29 percent by weight in the underflow non-volatile portion and triethanolamine is enriched from 1.81 percent by weight in the feed stream to 2.45 percent by weight in the underflow non-volatile portion. Examples I through V show similar monoethanolamine enrichment in the overhead volatile portion and enrichment of diethanolamine and triethanolamine in the underflow non-volatile portion under several different conditions of temperature and pressure. The operation of the separator in these Examples produced about 5 percent by weight to about 10 percent by weight of underflow non-volatile portion based on the total weight of the feed stream.

EXAMPLES VII THROUGH X

Purification of a Mixture of Polyamines

A reaction system and apparatus consisting of a separator identical to that described herein above were used in Examples VII through X. The separator was adjusted to a temperature and pressure given in Table B below for each Example. A liquid feed stream entering the separator was also adjusted to a flow rate specified for each Example in Table B. The liquid feed stream consisted of a mixture of ammonia, polyamines, sediment/gel and metals in amounts specified for each Example in Table B. The polyamines component in the liquid feed stream consisted of triethylenetetramine, tetraethylenepentamine, pentaethylenehexamine and other heavier polyamines made up of a mixture of linear and/or cyclic compounds formed by the addition of ethyl amino and/or piperazino organic radicals to the lower molecular weight compounds. The sediment/gel component in the liquid feed stream consisted of a bottom layer obtained by centrifugation of the crude liquid feed stream and includes metal salts, polyamines and water. The metals component in the liquid feed stream consisted of sodium, iron, chromium, nickel, and copper. The liquid feed stream entered the separator at the indicated temperature and pressure given in Table B and separation occurred, i.e., the liquid feed stream was separated into an overhead more volatile portion and an underflow less volatile portion due to density differences. A sample of the overhead more volatile portion removed from the separator as a liquid and a sample of the underflow less volatile portion removed from the separator as a gelatinous residue were then collected and analyzed by gas chromatography (polyamines), centrifugation (sediment/gel), and emission spectroscopy using the inductively Coupled Plasma technique (metals). The amount of ammonia was determined by a simple distillation technique. The relative amount of each component contained in the overhead more volatile portion and the underflow less volatile portion for each Example is given in Table B.

TABLE B
PURIFICATION OF A MIXTURE OF POLYAMINES PROCESS DATA

| | VII | VIII | IX | X |
|---|---|---|---|---|
| Phase Separation Conditions | | | | |
| Temperature, °C. | 155 | 140 | 150 | 110 |
| Pressure, psig | 2600 | 2600 | 2600 | 1500 |
| Feed Stream | | | | |
| Flow Rate, grams/hour | 3632 | 4078 | 4193 | 3999 |
| Ammonia, grams | 3015 | 3351 | 3644 | 3639 |
| Polyamines, grams | 609 | 716 | 539 | 349 |
| Sediment/Gel, grams | 8 | 10 | 10 | 11 |
| Metals, grams | .86 | .36 | .27 | .16 |
| Overhead More Volatile Portion | | | | |
| Production Rate, grams/hour | 3623 | 4066 | 4183 | 3987 |
| Ammonia, grams | 3015 | 3351 | 3644 | 3639 |
| Polyamines, grams | 609 | 715 | 539 | 349 |
| Sediment/Gel, grams | 0 | 0 | 0 | .03 |
| Metals, grams | .24 | .15 | .08 | .03 |
| Underflow Less Volatile Portion | | | | |
| Production Rate, grams/hour | 9 | 12 | 10 | 11 |
| Ammonia, grams | 0 | 0 | 0 | 0 |
| Polyamines, grams | 0 | 1 | 0.06 | 0 |
| Sediment/Gel, grams | 8 | 10 | 10 | 11 |
| Metals, grams | .62 | .21 | .19 | .13 |

Examples VII through X illustrate the overall effectiveness of the present invention in purifying mixtures containing polyamines. As can be seen from these Examples, a crude liquid feed stream consisting of a mixture of ammonia, polyamines, sediment/gel and metals may undergo separation at temperatures and pressures sufficient to essentially eliminate less desirable sediment/gel and metals from the mixture and thus enhance the purity of more desirable polyamines. The more desirable overhead more volatile portion consisting essentially of pure ammonia and polyamines may then undergo further processing and/or utilization and the less desirable underflow less volatile portion consisting essentially of sediment/gel and metals may be removed from the system as a gelatinous residue. It should be noted that a portion of the polyamines concentration in the feedstream sediment/gel may be separated therefrom to give a reduced amount of polyamines in the overhead more volatile sediment/gel, if any, and the underflow less volatile sediment/gel based on the total amount of polyamines in the feedstream sediment/gel, thus a further enrichment of polyamines may result in the overhead more volatile polyamines component. The enrichment of polyamines as illustrated in Example VII through X refers to the quality of the desirable overhead more volatile portion consisting essentially of ammonia and polyamines at the almost complete exclusion of less desirable sediment/gel and metals removed in the underflow less volatile portion.

We claim:

1. A process for the treatment of organic amine compositions which are under such temperature and pressure that with time at least a portion of the components thereof can undergo molecular chemical change and which can change desirable components and undesirable components, the desirable component being more volatile than the undesirable component, which process comprises arresting such molecular chemical change by subjecting such amine composition to a component separation at a pressure and temperature at which such more volatile component becomes, during separation, a supercritical fluid and the amine composition is converted into a multi-phase system, forming from such separation two enriched streams, one which is more enriched in the more volatile amine components of such amine composition than is such amine composition, and the other of which is less rich in such more volatile amine components than is said other stream and such amine composition but more enriched in the less volatile components of the amine composition than is said other stream and the amine composition.

2. The process of claim 1 wherein the organic amine composition comprises ammonia, monoethanolamine, diethanolamine, triethanolamine and water.

3. The process of claim 2 wherein the two enriched streams consist of a more volatile stream enriched in monoethanolamine and a less volatile stream enriched in diethanolamine and triethanolamine.

4. The process of claim 1 wherein the organic amine composition comprises ammonia, polyamines, sediment/gel and metals.

5. The process of claim 4 wherein the two enriched streams consist of a more volatile stream enriched in polyamines and a less volatile stream enriched in sediment/gel and metals.

6. The process of claim 4 wherein the polyamines component comprises triethylene tetramine, tetraethylene pentamine, pentaethylenehexamine, and other heavier polyamines made up of a mixture of linear and cyclic compounds formed by the addition of ethylamino and piperazino organic radicals to the lower molecular weight compounds.

* * * * *